United States Patent [19]

de Nanteuil et al.

[11] Patent Number: 5,468,761

[45] Date of Patent: Nov. 21, 1995

[54] 4-METHYL-5-SUBSTITUTED-1,3-OXAZOLES HAVING ANTI-INFLAMMATORY ACTIVITY

[75] Inventors: Guillaume de Nanteuil, Suresnes; Michel Vincent, Bagneux; Christine Lila, Viroflay; Jacqueline Bonnet, Paris; Armel Fradin, Neuilly Sur Seine, all of France

[73] Assignee: Adir et Compagnie, Courbevoie, France

[21] Appl. No.: 164,464

[22] Filed: Dec. 9, 1993

[30] Foreign Application Priority Data

Dec. 11, 1992 [FR] France .................. 92 14912

[51] Int. Cl.[6] .................................................. A61K 31/42
[52] U.S. Cl. ........................................ 514/374; 548/236
[58] Field of Search ............................ 514/374; 548/236

[56] References Cited

U.S. PATENT DOCUMENTS

| 3,574,228 | 4/1971 | Brown | 548/236 |
|---|---|---|---|
| 3,579,529 | 5/1971 | Brown | 548/236 |
| 3,869,468 | 3/1975 | Tarzia | 548/236 |
| 4,596,816 | 6/1986 | Meguro | 514/374 |
| 4,774,253 | 9/1988 | Machin et al. | 548/236 |

FOREIGN PATENT DOCUMENTS 92-12141  7/1992  WIPO .................. 548/236

Primary Examiner—Donald G. Daus
Attorney, Agent, or Firm—Gordon W. Hueschen

[57] ABSTRACT

Compound of formula (I):

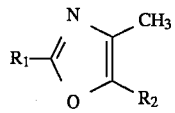

in which:

$R_1$ represents 1-adamantyl, dicyclopropylmethyl, substituted or unsubstituted ($C_3$–$C_6$) cycloalkyl or substituted or unsubstituted bicyclo[2.2.2]oct-1-yl, $R_2$ represents:

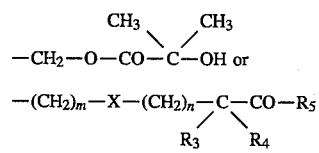

in which:

m represents 1, 2 or 3,

X represents oxygen or sulfur or N—R, $R_3$ or $R_4$, which are identical or different, represent hydrogen, ($C_1$–$C_6$) alkyl or trifluoromethyl,

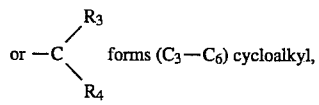

n represents 0, 1 or 2, $R_5$ represents hydroxy, or ($C_1$–$C_6$) alkoxy, and anti-inflammatory medicinal products containing the same.

5 Claims, No Drawings

4-METHYL-5-SUBSTITUTED-1,3-OXAZOLES HAVING ANTI-INFLAMMATORY ACTIVITY

The present invention relates to new 4-methyl-1,3-oxazole compounds.

These compounds, in addition to the fact that they are new, possess pharmacological properties which render them usable in the treatment of arthritis and inflamatory pathologies.

During the inflamatory reaction, substantial modifications occur in the synthesis of a group of plasma proteins called acute-phase proteins. Some of these proteins—including fibrinogen, reactive protein C, haptoglobin—are increased during the acute-phase reaction, whereas others such as albumin and transferrin are reduced. The alteration of these proteins, in particular fibrinogen, is responsible for the modifications in the plasma viscosity and for the increase in the speed of sedimentation which are observed in the inflamation. Because of their correlation with clinical parameters during the development and the therapeutic remissions observed in rheumatoid arthritis, some of these acute-phase proteins have been used as a criterion for evaluating the disease (Mallya R. K. et al., J. Rheumatol., 1982, 9, 224–8; Thompson P. W. et al., Arthritis Rheum 1987, 30, 618– 23). They are under the dependence of certain cytokines, in particular $Il_1$ and $Il_6$, which are recognised as playing an important role in arthritic pathology (Gauldie J et al., Cytokines and acute phase protein expression. In : Cytokines and Inflammation. Edited by E. S. Kimball. CRC Press, 1991, p 275–305).

In animal pharmacology, the modifications of the acute-phase proteins have been studied, in particular, in rats during the acute inflammatory phase following the injection of complete adjuvant (Lewis E. J. et al., J. Pharmacol Meth 1989, 21, 183– 94).

A certain number of 1,3-oxazole compounds have been described in the literature. Such is the case, in particular, for the compounds described in Patent EP 220573 (corresponding to U.S. Pat. No. 4,774,253).

More specifically, the present invention relates to the compounds of formula (I):

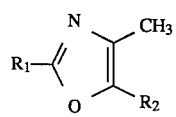

in which:

R$_1$ represents a 1-adamantyl group, a dicyclopropylmethyl group, a (C$_3$–C$_6$) cycloalkyl group (unsubstituted or substituted by a halogen atom, a hydroxy group, or a linear or branched (C$_1$–C$_6$) alkoxy group) or a bicyclo [2.2.2]oct-1-yl group (unsubstituted or substituted at the 4-position by a halogen atom, a linear or branched (C$_1$–C$_6$) alkoxy group or a hydroxy group), R$_2$ represents a group

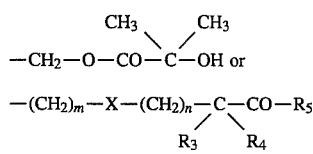

in which:

m represents 1, 2 or 3,

X represents an oxygen or sulfur atom or an N—R group (in which R is a hydrogen atom or a linear or branched (C$_1$–C$_6$) alkyl group), R$_3$ or R$_4$, which are identical or different, represent a hydrogen atom, a linear or branched (C$_1$–C$_6$) alkyl group, a trifluoromethyl group, or

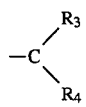

forms a (C$_3$–C$_6$) cycloalkyl radical, n represents 0, 1 or 2

R$_5$ represents a hydroxy group, a linear or branched (C$_1$–C$_6$) alkoxy group, an amino group (unsubstituted or substituted by one or two linear or branched (C$_1$–C$_6$) alkyl groups), or —O—CH$_2$—CO—NRR' (such that R and R' represent a linear or branched (C$_1$–C$_6$) alkyl group, or form with the nitrogen atom carrying them a 5- or 6-membered heterocycle), their enantiomers, diastereoisomers or epimers as well as their addition salts with a pharmaceutically acceptable acid or base.

Among the pharmaceutically acceptable acids, there may be mentioned, with no limitation being implied, hydrochloric, sulfuric, tartaric, maleic, fumaric, methanesulfonic and camphoric acids and the like.

Among the pharmaceutically acceptable bases, there may be mentioned, with no limitation being implied, sodium hydroxide, potassium hydroxide, tert-butylamine, diethylamine, ethylenediamine and the like.

The invention also extends to the process for preparing the compounds of formula (I), wherein there is used as starting material an acid of formula (II):

in which R$_1$ has the same meaning as in formula (I), which is reacted with ethyl 2-chloroacetoacetate, to give the compound of formula (III),

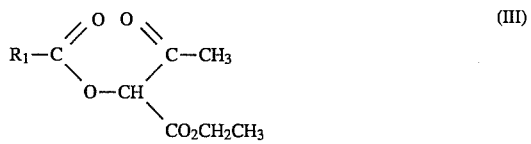

in which R$_1$ has the same meaning as in formula (I), which is subjected to the action of formamide in acidic medium, to give the compound of formula (IV):

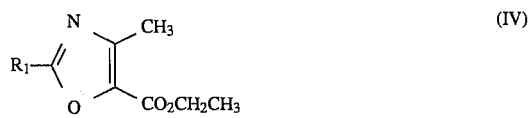

in which R$_1$ has the same meaning as in formula (I), which is converted:

to the compound of formula (V) by reduction in the presence of lithium aluminum hydride,

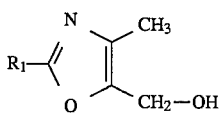 (V)

in which $R_1$ has the same meaning as in formula (I), which is reacted with:
either, in anhydrous medium, acetone in the presence of dried sodium hydroxide and of chloroform,
to give the compound of formula (I/a), which is a specific example of the compounds of formula (I):

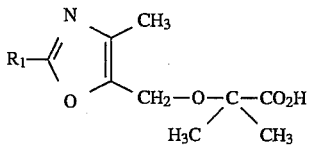 (I/a)

in which $R_1$ has the same meaning as in formula (I), whose acid functional group is converted, if desired, to an ester or amide functional group according to conventional organic chemistry techniques,
or, thionyl chloride, to give the compound of formula (VI):

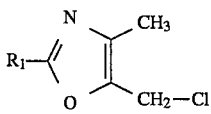 (VI)

in which $R_1$ has the same meaning as in formula (I), which may be reacted, if desired, with ethyl 2-hydroxyisobutyrate, in the presence of sodium hydride in nonanhydrous dimethylformamide medium, to give the compound of formula (I/b):

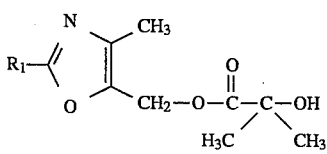 (I/b)

in which $R_1$ has the same meaning as in formula (I), which compound of formula (VI) may be subjected to conventional organic chemistry reactions to give the compound of formula (VII):

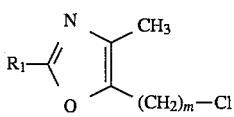 (VII)

in which $R_1$ and m have the same meaning as in formula (I), which is reacted:
 a with a compound of formula (VIII), in DMF, in anhydrous medium:

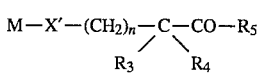 (VIII)

in which M represents an alkali metal, n, $R_3$, $R_4$ and $R_5$ are as defined in formula (I), $R_5$ being linear or branched $(C_1-C_6)$ alkoxy, and X' represents a sulfur or oxygen atom, to give the compound of formula (I/c), which is a specific example of the compounds of formula (I),

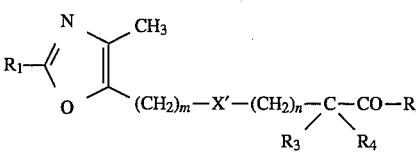 (I/c)

in which $R_1$, $R_3$, $R_4$, $R_5$, X', m and n are as defined above, in which $R_5$ is converted, if desired, to the corresponding hydroxy group by saponification and, when it represents a hydroxy group, to the corresponding amino or ester group according to conventional organic chemistry techniques,
 b with an amino ester of formula (IX):

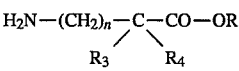 (IX)

in which R represents an alkyl group, n, $R_3$ and $R_4$ have the same meaning as in formula (I), to give the compound of formula (I/d), which is a specific example of the compounds lo of formula (I):

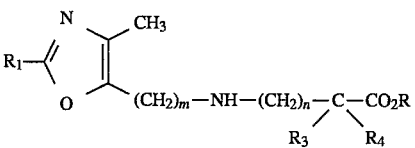 (I/d)

in which $R_1$, $R_3$, $R_4$, R, m and n have the same meaning as above,
whose ester functional group is converted, if desired, to the corresponding acid functional group and then to the amide functional group according to conventional organic chemistry techniques and whose secondary amine functional group is converted, if desired, to a tertiary amine functional group by alkylation,
which compounds of formula (I/a), (I/b), (I/c) or (I/d) are purified, where appropriate, according to a conventional purification technique, whose isomers are separated, if desired, according to conventional separation techniques, and which are optionally converted to their addition salts with a pharmaceutically acceptable acid or base.

These new 4-methyl-1,3-oxazole compounds have very useful pharmacological properties. They reduce the effects of an injection of Freund's adjuvant in rats both at the level of the acute-phase plasma proteins (albumin) and the local edema. This effect indicates an anti-inflammatory activity of the compounds of the invention.

The invention also extends to the pharmaceutical compositions containing, as active ingredient, at least one compound of formula (I) or its optical isomers with one or more inert, non-toxic and appropriate excipients. The pharmaceutical compositions obtained can be provided in various forms, the most advantageous being tablets, sugar-coated tablets, hard gelatin capsules, suppositories, suspensions to be taken orally, the transdermal forms (gel, patch), and the like.

The useful dosage can be adjusted according to the nature and severity of the condition, the route of administration as well as according to the age and the weight of the patient. This unit dosage ranges from 0.02 g to 2 g per day in one or more doses.

The following examples illustrate the invention but do not limit it in any manner.

The starting materials used are starting materials which are known or which are prepared according to known procedures.

EXAMPLE 1

2-Methyl-2-{[2-(adamant-1-yl)-4-methyl-1,3-oxazol-5-yl]methoxy}propionic acid, sodium salt Stage A: Ethyl 2-[(adamant-1-yl)carbonyloxy]acetoacetate 200 mmol of 1-adamantanecarboxylic acid are added to 100 mmol of sodium carbonate placed in 160 ml of DMF. The mixture is heated to 80° C. and then 200 mmol of ethyl 2-chloroacetoacetate in solution in 40 ml of DMF are added. The temperature and the stirring are maintained for three hours and then the mixture is left for 10 hours at room temperature. After evaporation of the DMF, the residue is taken up in 300 ml of water and 300 ml of ether. After extraction, drying and evaporation, the expected product is obtained in the form of an oil.

Stage B: 2-(Adamant-1-yl)-4-methyl-5-ethoxycarbonyl-1,3-oxazole 3.8 ml of concentrated sulfuric acid, then 33 mmol of the product obtained in the preceding stage, are added, dropwise, at 10° C., to 27.7 ml of anhydrous formamide. The mixture is heated for 2 hours at 140° C. After cooling to 10° C., 140 ml of water and 100 ml of ether are added. After extraction, washing of the organic phase with N/10 sulfuric acid, drying and evaporation, the expected product is obtained after silica column purification, using as eluent a dichloromethane/ethyl acetate mixture (95/5).

Elemental microanalysis:

|  | C % | H % | N % |
| --- | --- | --- | --- |
| calculated | 70.56 | 8.01 | 4.84 |
| found | 70.59 | 7.78 | 5.18 |

Stage C: 2-(Adamant-1-yl)-4-methyl-5-hydroxymethyl-1,3-oxazole 30 mmol of lithium aluminum hydride are placed, under a nitrogen atmosphere, in 40 ml of THF, at 0° C. 23 mmol of the compound obtained in the preceding stage are added to this mixture and the whole mixture is left for one hour at 0° C. and then for 2 hours at room temperature. 7.5 ml of isopropanol and 4.5 ml of a saturated sodium chloride solution are then added and the mixture is then left for 10 hours at room temperature. After filtration of the precipitate, the filtrate is evaporated and the residue taken up in 50 ml of water and 150 ml of ether. After extraction, washing, drying and evaporation, the expected product is obtained in the form of white crystals.

Melting point: 134° C.

Elemental microanalysis:

|  | C % | H % | N % |
| --- | --- | --- | --- |
| calculated | 72.84 | 8.56 | 5.66 |
| found | 72.72 | 8.58 | 5.70 |

Stage D: 2-Methyl-2-{[2-(adamant-1-yl)-4-methyl-1,3-oxazol-5-yl]methoxy}propionic acid, sodium salt 18 mmol of the compound obtained in the preceding stage are placed in 27 ml of anhydrous acetone. 92 mmol of dry and powdered sodium hydroxide are then added. The mixture is heated at the reflux temperature of acetone until a red colour is obtained. 24 mmol of chloroform in 5.5 ml of acetone are added and the medium is refluxed for 4 hours and then brought to room temperature for 10 hours. After evaporation of the solvent, the residue is taken up in 200 ml of water and washed with 200 ml of ether. The aqueous phase is then acidified with 2N $HC_1$ up to pH=2. The precipitate is filtered, dried and washed and is converted to the corresponding sodium salt.

Elemental microanalysis:

|  | C % | H % | N % |
| --- | --- | --- | --- |
| calculated | 64.21 | 7.37 | 3.94 |
| found | 64.02 | 7.35 | 3.87 |

EXAMPLE 2

Ethyl 2-methyl-2-{[2-(dicylopropylmethyl)-4-methyl-1,3-oxazol-5-yl]methoxy}propionate Stages A, B and C are identical to stages A, B and C of Example 1: 1-adamantanecarboxylic acid being replaced in stage A by dicyclopropylmethylcarboxylic acid.

Stage D: 2-(1-Dicyclopropylmethyl)-4-methyl-5-chloromethyl-1,3-oxazole 22 mmol of the compound obtained in the preceding stage in 50 ml of dichloromethane are cooled to 5° C. 3.25 ml of thionyl chloride are then added dropwise. The mixture is refluxed for 2 hours. The expected product is then obtained in the form of an oil after evaporation and drying.

Stage E: Ethyl 2-methyl-2-{[2-(dicyclopropylmethyl)-4-methyl-1,3-oxazol -5-yl]methoxy}propionate 51 mmol of sodium hydride are placed in 40 ml of anhydrous DMF under a nitrogen atmosphere. 51 mmol of ethyl 2-hydroxyisobutyrate in 20 ml of DMF are then added and the mixture is left for one hour at room temperature. After cooling on an ice bath, 36 mmol of the compound obtained in the preceding stage in solution in 20 ml of DMF are added. The mixture is stirred overnight at room temperature. At −5° C., 20 ml of a saturated ammonium chloride solution are added. After evaporation of the DMF, taking up in 150 ml of water, extraction with ethyl acetate, washing and drying, the expected product is obtained in the form of an oil after evaporation and purification by silica column chromatography, using as eluent a pentane/ethyl acetate mixture (85/15).

Elemental microanalysis:

|  | C % | H % | N % |
| --- | --- | --- | --- |
| calculated | 67.26 | 8.47 | 4.36 |
| found | 67.42 | 8.48 | 4.70 |

EXAMPLE 3

2-Methyl-2-{[2-(dicyclopropylmethyl)-4-methyl-1,3-oxazol -5-yl]methoxy}propionic acid, sodium salt 8 mmol of sodium hydroxide pellets, then 4 ml of water, are added to a solution containing 8 mmol of the product obtained in the preceding stage in 60 ml of ethanol. The mixture is refluxed for 3 hours. After evaporation, taking up of the residue in water, extraction with ether and acidification with 4N hydrochloric acid, the expected product is obtained after filtration and drying and is converted to the corresponding sodium salt.

Elemental microanalysis:

|  | C % | H % | N % |
|---|---|---|---|
| calculated | 60.94 | 7.03 | 4.44 |
| found | 60.99 | 7.02 | 4.79 |

Examples 4 and 6 were synthesized according to the same procedure as that described for Example 2.

Examples 5 and 7 were synthesized according to the same procedure as that described for Example 3.

EXAMPLE 4

Ethyl 2-methyl-2-{[2-(4-methoxycyclohexyl)-4-methyl-1,3-oxazol-5-yl]methoxy}propionate

EXAMPLE 5

2-Methyl-2-{[2-(4-methoxycyclohexyl)-4-methyl-1,3-oxazol-5-yl]methoxy}propionic acid, sodium salt Mass spectrum: FAB: $[M+H]^+$: m/z=334

EXAMPLE 6

Ethyl 2-methyl-2-{[2-(bicyclo[2.2.2]oct-1-yl)-4-methyl-1,3-oxazol-5-yl]methoxy}propionate

EXAMPLE 7

2-Methyl-2-{[2-(bicyclo[2.2.2]oct-1-yl)-4-methyl-1,3-oxazol-5-yl]methoxy}propionic acid, sodium salt

EXAMPLE 8

2-(Adamant-1-yl)-4-methyl-5-(2-hydroxyisobutyroxymethyl)-1,3-oxazole

Stages A to D of this example are carried out according to the same procedures as those described in stages A to D of Example 2.

Stage E: 2-(Adamant-1-yl)-4-methyl-5-(2-hydroxyisobutyroxymethyl)-1,3-oxazole 29 mmol of sodium hydride are placed in 20 ml of DMF. At 0° C., 29 mmol of ethyl 2-hydroxyisobutyrate in solution in 10 ml of non-anhydrous DMF are added and the mixture is left for one hour at room temperature. 21 mmol of the product obtained in the preceding stage are poured in Udropwise, at 0° C., and the stirring is maintained for 10 hours at room temperature. After hydrolysis at 5° C. with 20 ml of a saturated aqueous ammonium chloride solution, the DMF is evaporated and the residue is taken up in 100 ml of water and extracted with 100 ml of ether. The expected product is obtained after silica column purification, using as eluent a pentane/ethyl acetate mixture (80/20).

Melting point: 68°–70° C.

Elemental microanalysis:

|  | C % | H % | N % |
|---|---|---|---|
| calculated | 68.44 | 8.16 | 4.20 |
| found | 68.55 | 8.16 | 4.47 |

Pharmacological Study of the Compounds of the Invention

EXAMPLE 9

Activity in vivo on the acute-phase proteins

The biological activity of the compounds of the invention was determined in particular on the plasma albumin of rats 6 days after subcutaneous injection of complete Freund's adjuvant. Negative protein of the acute phase of the inflammation, albumin, which is substantially reduced by the inflammatory state which follows the adjuvant, is completely or partially restored by the compounds administered at the daily oral dose of 100 mg/kg.

Experimental procedure

Adjuvant arthritis in rats, described for the first time by Pearson (Pearson C. M., Proc. Soc. Exp. Biol. Med., 1956, 91, 95–101) was caused by injecting 0.1 ml of complete Freund's adjuvant (4 mg of Mycobacterium butyricum in suspension in 1 ml of paraffin oil/water/Tween 80) into the subplantar region of the hind legs of Lewis female rats (aged 62 days).

The products were administered daily in the form of an aqueous solution or of a suspension in hydroxypropyl cellulose at 0.2% according to their solubility.

Their activity on the acute-phase proteins was evaluated by determining the plasma levels of albumin 6 days after the induction of arthritis (colorimetric assay method described by Lewis (Lewis E. J. et al., J. Pharmacol. Meth. 1989, 21, 183– 94), the adjuvant itself causing a drop of 31% in the basal albumin level. The clinical effect was assessed by plethysmometric measurement of the volume of the infected hind leg.

The activity of the compounds of the invention is very much superior to that of a reference compound: romazarit, as shown by the results presented below:

|  | hypoalbuminemia correction |
|---|---|
| Example 1: 31% | 31% |
| Example 2: 47% | 47% |
| Example 3: 27% | 27% |
| romazarit: 1% | 1% |

At the same time, the compounds tend to reduce the intensity of the edema at the site of injection. Accordingly, compound 2 reduces the edema by 9%.

EXAMPLE 10

Pharmaceutical composition

Preparation formula for 1000 tablets in 20 mg doses

| | |
|---|---|
| Compound of Example 1 | 20 g |
| Hydroxypropyl cellulose | 2 g |
| Wheat starch | 10 g |
| Magnesium stearate | 100 g |
| Talc | 3 g |

We claim:

1. A compound selected from those of formula (I):

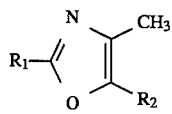

in which:

$R_1$ represents 1-adamantyl; dicyclopropylmethyl; $(C_3-C_6)$ cycloalkyl which is unsubstituted or substituted by halogen, hydroxy, or linear or branched $(C_1-C_6)$ alkoxy; or bicyclo[2.2.2]oct-1-yl which is unsubstituted or substituted at the 4-position by halogen, linear or branched $(C_1-C_6)$ alkoxy, or hydroxy;

$R_2$ represents:

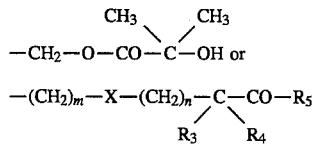

in which:

m represents 1, 2 or 3,

X represents oxygen or sulfur or N—R in which R is hydrogen or linear or branched $(C_1-C_6)$ alkyl, $R_3$ or $R_4$, which are identical or different, represent hydrogen, linear or branched $(C_1-C_6)$ alkyl, trifluoromethyl, or the group

forms $(C_3-C_6)$ cycloalkyl, n represents 0, 1 or 2, $R_5$ represents hydroxy a linear or branched $(C_1-C_6)$ alkoxy, which is unsubstituted or substituted by one or two linear or branched $(C_1-C_6)$ alkyl;

its enantiomers, diastereoisomers or epimers to its addition salts with a pharmaceutically acceptable acid or base.

2. A compound of in claim 1, selected from those wherein $R_1$ represents 1-adamantyl, its enantiomers, diastereoisomers and epimers and its addition salts with a pharmaceutically-acceptable acid or base.

3. A compound of claim 1, $R_1$ represents dicyclopropylmethyl, its enantiomers, diastereoisomers and epimers and its addition salts with a pharmaceutically acceptable acid or base.

4. A method for treating a mammal afflicted with arthritis or an inflammatory disease comprising the step of administering to the mammal an amount of a compound of claim 1 which is effective for alleviation of said condition.

5. A pharmaceutical composition useful in the treatment of arthritis or inflammatory diseases comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,468,761

DATED : November 21, 1995

INVENTOR(S) : Guillaume de Nanteuil, et al

It is certified that error appears in the above-indentified patent and that said Letters Patent is hereby corrected as shown below:

Column 4, line 21 (approx.): Delete "lo".

Column 6, line 21: Add a -- - -- (dash) to end of line.

Column 6, line 22: Delete " - " at beginning of the line.

Column 7, line 36: "[2.2.21" should read -- [2.2.2] --.

Column 10, line 16: "hydroxy a" should read -- hydroxy or --.
(Claim 1, line 1).

Column 10, lines 17 & 18: Delete line starting with "which is ......alkyl;".

Column 10, line 19: "epimers to" should read -- epimers and --.
Claim 1, line 7.

Column 10, line 20: Add a -- - -- (dash) after "pharmaceutically".
Claim 1, line 8:.

UNITED STATES PATENT AND TRADEMARK OFFICE
CERTIFICATE OF CORRECTION

PATENT NO. : 5,468,761
DATED : November 21, 1995
INVENTOR(S) : Guillaume de Nanteuil, et al It is certified that error appears in the above-indentified patent and that said Letters Patent is hereby corrected as shown below:

Column 10, line 21: Delete "in".

Column 10, line 25: Insert after claim 1, -- selected from those wherein --.

Column 10, line 27: Add a -- - -- (dash) after "pharmaceutically".
Claim 3, line 4.

Signed and Sealed this

Fifth Day of March, 1996

*Attest:*

BRUCE LEHMAN

*Attesting Officer*  *Commissioner of Patents and Trademarks*